United States Patent
Hölscher et al.

(10) Patent No.: US 10,745,645 B2
(45) Date of Patent: Aug. 18, 2020

(54) 4-ETHYL-OCTENE-2/3-NITRILE AS A FRAGRANCE

(71) Applicant: SYMRISE AG, Holzminden (DE)

(72) Inventors: Bernd Hölscher, Halle (DE); Tobias Wagner, Hellental (DE)

(73) Assignee: SYMRISE AG, Holzminden (DE)

(*) Notice: Subject to any disclaimer, the term of this patent is extended or adjusted under 35 U.S.C. 154(b) by 0 days.

(21) Appl. No.: 16/606,247

(22) PCT Filed: Apr. 21, 2017

(86) PCT No.: PCT/EP2017/059479
§ 371 (c)(1),
(2) Date: Oct. 18, 2019

(87) PCT Pub. No.: WO2018/192665
PCT Pub. Date: Oct. 25, 2018

(65) Prior Publication Data
US 2020/0123466 A1    Apr. 23, 2020

(51) Int. Cl.
*A61K 8/00* (2006.01)
*A61K 8/18* (2006.01)
*A61Q 13/00* (2006.01)
*C11B 9/00* (2006.01)

(52) U.S. Cl.
CPC ................. *C11B 9/0023* (2013.01)

(58) Field of Classification Search
CPC ............. A61K 8/00; A61K 8/18; A61Q 13/00
USPC ........................................ 512/6, 1
See application file for complete search history.

(56) References Cited

U.S. PATENT DOCUMENTS

| 2,352,515 A | 6/1944 | Bruson |
| 4,156,690 A | 5/1979 | Desimone |
| 2010/0279917 A1* | 11/2010 | Mane ................ C07C 255/03 512/6 |

FOREIGN PATENT DOCUMENTS

| EP | 0395982 A2 | 11/1990 |
| EP | 1413570 A1 | 4/2004 |
| WO | 2008037105 A1 | 4/2008 |

OTHER PUBLICATIONS

International Search Report and Written Opinion dated Jul. 7, 2017 for corresponding PCT Application No. PCT/EP2017/059479.
James W. Wilt et al., "Cyanomethylidenebis(tryphenylphosphonium)Dibromide. Its Use in a Convenient Modification of the Witting Reaction", Journal of Organic Chemistry, vol. 36, No. 14, 1971, pp. 2026-2027 XP055379320.
Yoshiro Sato and Yasuko Niinomi, "Selective Synthesis of (Z)-Alk-2-enenitriles from Aldehydes", Journal of the Chemical Society, Chemical Communications, No. 1, 1982, pp. 56-57 XP002771374.

* cited by examiner

*Primary Examiner* — Jessica Whiteley
(74) *Attorney, Agent, or Firm* — Polsinelli PC

(57) ABSTRACT

The present invention primarily relates to the use of 4-ethyl-octen-2-nitrile and/or 4-ethyl-octen-3-nitrile as fragrance. The invention further relates to novel fragrance compositions comprising 4-ethyl-octen-2/3-nitrile, perfumed products comprising 4-ethyl-octen-2/3-nitrile as well as diverse methods for imparting, modifying and/or enhancing certain scents.

19 Claims, No Drawings

4-ETHYL-OCTENE-2/3-NITRILE AS A FRAGRANCE

CROSS-REFERENCE TO RELATED APPLICATIONS

This application is a national stage application (under 35 U.S.C. § 371) of PCT/EP2017/059479, filed Apr. 21, 2017, which is incorporated herein by reference in its entirety.

The present invention primarily relates to the use of 4-ethyl-octen-2-nitrile and/or 4-ethyl-octen-3-nitrile, i.e. a compound of formula (I) as described herein, as a fragrance. The invention further relates to novel fragrance compositions comprising 4-ethyl-octen-2/3-nitrile, perfumed products comprising 4-ethyl-octen-2/3-nitrile as well as several methods for imparting, modifying and/or enhancing distinct scents.

Further aspects and preferred embodiments of the present invention emerge from the following aspects, the attached examples and particularly the attached claims.

Although a plurality of fragrances is already available, a general need of novel fragrances still exists in the perfume industry. Thus, a need of fragrances, which are capable of imparting further interesting scents in addition to a primary scent and of advancing a perfumer's possibilities due to their novel or, respectively, original olfactory characteristics, exists. Particularly, there is an interest in fragrances with scents which are capable of joining a combination with flowery and/or fruity fragrances. Preferably in such a case, an overlap of the different olfactory aspects and scents is achieved to thus provide a complex olfactory impression.

For the creation of novel compositions, there is a constant need of fragrances with special sensory characteristics, which are suitable to serve as a basis for the composition of novel perfumes with complex sensory character. Preferred desired fragrances shall, in addition to a certain scent, exhibit further scents and aspects which impart them a character and complexity.

The search for suitable substances which led to the present invention was further impeded by the following circumstances:

- the mechanisms of the olfactory perception are not sufficiently known;
- the relationship between the special olfactory perception on the one side and the chemical structure of the corresponding fragrance on the other side are not sufficiently investigated;
- often, minor changes in the structural composition of a known fragrance cause substantial changes in the sensory characteristics and impair the tolerance of the human organism.

The primary aspect was thus to find fragrances which exhibit an interesting, preferably complex, and original sensory profile and which are suitable as fragrance for the use in e.g. the perfumery or other areas, where applicable also in edible compositions.

Within the scope of the present invention, particularly substances were desired which can exhibit or, respectively, impart, modify and/or enhance one, several or all of the scents green, flowery and woody. Particularly such substances should be identified which preferably can exhibit and/or impart at least one of the scents green, nitrile, rosy like iris and carrot scent.

The desired substances should enable the production of novel fragrance compositions with special olfactory scents and aspects. Advantageous are such substances which are particularly suitable for being combined with further fragrances, which exhibit one or more of the scents green, nitrile, and/or rosy like iris and carrot scent.

In addition, these fragrances fulfilling the primary object preferably further have additional positive secondary characteristic such as e.g. a high stability at certain conditions of application, a high extensiveness, a high ability to adhere, a high substantivity or scent enhancing characteristics (so-called booster or enhancer effect) in addition to their primary, i.e. olfactory, characteristics, and/or complement the authenticity, freshness, fullness, power and/or charisma of further fragrances when being combined with these, such that sensorial remarkable effects may be obtained.

The primary object is achieved by the use of 4-ethyl-octen-3-nitrile (4-ethyl-oct-3-en-nitrile; formula (Ia); cf. e.g. CAS-No. 29127-85-3) and/or 4-ethyl-octen-2-nitrile (4-ethyl-oct-2-en-nitrile; formula (Ib); cf. e.g. CAS-No. 82125-04-0), i.e. one or more or, respectively, both compound(s) of formula (I) (4-ethyl-octen-2/3-nitrile)

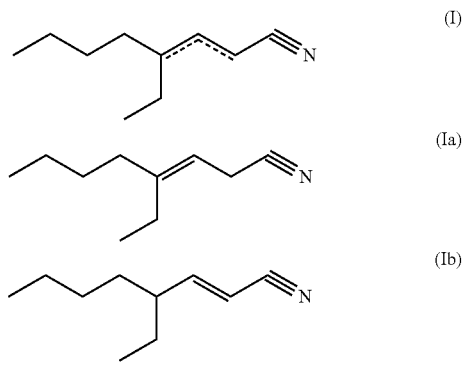

as a fragrance (or, respectively, fragrance composition). Within the scope of the present invention, a compound of formula (Ia), a compound of formula (Ib) or—preferably—a mixture of a compound of formula (Ia) and a compound of formula (Ib) may be used or, respectively, applied. A compound of formula (I) or, respectively, (Ia) or (Ib) to be used according to the invention may be present as any stereoisomeric form, i.e. configuration (entantiomers, cis/trans isomers) or, respectively, conformation, or, respectively, may be present as any mixture of stereoisomers (e.g. E/Z mixture).

If within this text any inconsistency between the chemical name and the presented structures may occur, the presented structures apply.

What was said herein with regard to a compound of formula (I), particularly the advantages described herein, also apply for the preferred mixture of a compound of formula (Ia) and a compound of formula (Ib) to be used or, respectively, to be applied (cf. above).

A compound of formula (I) has autonomous olfactory characteristics which clearly differ from and surpass the known fragrances. The suitability of the compounds of formula (I) as fragrances was currently not known. It is thus particularly surprising that on the already well explored field a fragrance with valuable, interesting and complex olfactory characteristics could be found.

Preferably, the use according to the invention relates to a use for imparting, modifying and/or enhancing one or more scents selected from the group consisting of the scents green, nitrile, herbaceous, fresh, fruity, flowery, rosy, woody, sweet, earthy, fatty, metallic, balsam and iris and carrot scents, preferably at least one of the scents selected from the group consisting of the scents green, nitrile, rosy and iris and carrot scents, preferably rosy with iris and carrot scents.

The fact that a compound of formula (I) according to the invention may impart a very complex and diverse sensory total impression, which otherwise may typically only be achieved by mixtures of several components (such as essential oils or spice mixtures), is very surprising.

In addition to the primary, i.e. olfactory, characteristics, the compounds of formula (I) also have positive secondary characteristics, particularly a high ability to adhere and a high substantivity compared to fragrances with similar olfactory characteristics as well as a high stability in certain media and compositions, a high extensiveness and are also biologically degradable.

A compound of formula (I) to be used according to the invention particularly has in largely neutral, however particularly in alkaline and/or oxidising media a high very excellent stability. Particularly due to this characteristic, the compounds of formula (I) are particularly suitable for being used as fragrances, particularly if used in perfumed products or compositions which have a pH value of 5.5 or higher, preferably of higher than or equal 6, preferably of higher than 7, further preferably of higher than 7.5, particularly preferably of higher than 8; further in compositions with an oxidising effect which preferably have a pH value of higher than or equal 7, preferably in compositions with an oxidising effect with a pH value of higher than or equal 8. The indicated pH values relate to values measured at 25° C.

In connection with the preferred use for imparting, modifying and/or enhancing a scent as described herein, is the finding that the compounds of formula (I) may excellently act as so-called boosters (or enhancers).

Thus, the use for or, respectively, a method for modifying and/or enhancing (boosting) a smell with one, several or all of the scents as described herein, preferably the scent(s) flowery, fruity and/or woody is provided, comprising the following step:

mixing one or more fragrances with one, several or all of the scents described herein, preferably the scent(s) flowery, fruity and/or woody with an amount of compound(s) of formula (I) which is sufficient to sensorically modify and/or enhance the olfactory impression of the fragrance(s) or, respectively, said scent(s).

A compound of formula (I) to be used according to the invention may also enhance the intensity of a fragrance mixture (fragrance composition) and complement with respect to the smell the overall impression of the mixture. The compounds described herein may thus be used to provide more fullness, freshness power, charisma, brilliance, complementation, harmony and/or authenticity of a fragrance composition.

Further, compounds of formula (I) are suitable as agent for enhancing the substantivity and/or retention of a fragrance mixture and/or as a fixator.

The production of a compound of formula (I) to be used according to the invention may be obtained by known reactions and methods. As is known to the skilled person, a compound of formula (I) may be obtained by a Knoevenagel reaction with cyano acetic acid and 2-ethyl hexanal with corresponding catalysts and the corresponding conditions (the educts to be used are commercially available).

A compound of formula (I) to be used according to the invention is typically used in a sensorically effective amount with regard to the use according to the invention, i.e. in a total amount in which it evokes a sensory effect. Preferably, the compound of formula (I) to be used according to the invention is applied together with further fragrances. Such fragrance compositions may be produced in a common way, e.g. by simple mixing or homogenizing of the components. The further fragrances may be any further fragrances.

A further aspect of the present invention thus relates to a fragrance composition comprising or consisting of one or more compound(s) of formula (I)

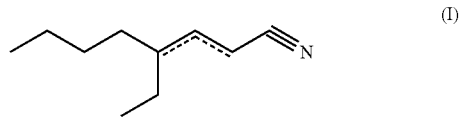

(I)

and one, two, three, four, five, six, seven, eight, nine, ten or more further fragrance(s), wherein in a fragrance composition according to the invention, the weight ratio of the total amount of compound(s)n of formula (I) to the total weight of further fragrance(s) is in a range of from 1:1000 to 1:0.1, preferably of from 1:1000 to 1:0.5.

It is preferred that the total amount of compound(s) of formula (I), related to the total weight of the fragrance composition, is in a range of from 0.0001 to 99.9 wt.-%, preferably 0.001 to 99.5 wt.-%, particularly preferably 0.01 to 99 wt.-%, 0.01 to 90 wt.-%, 0.05 to 80 wt.-%, 0.1 to 70 wt.-%, 0.25 to 50 wt.-%, 0.5 to 40 wt.-% or 0.75 to 25 wt.-%.

If a compound of formula (I) is mainly used for providing more power, complementation, harmony and/or authenticity to a fragrance composition and/or to enhance certain scents (cause by further fragrances), the total amount of compounds of formula (I) may also be selected comparatively low and e.g. be preferably in the range of from 0.01 to 5 wt.-%, further preferably in the range of from 0.1 to 2 wt. %, related to the total amount of the fragrance composition. If within the preferred concentration ranges a comparatively low concentration is selected, it may be possible in some cases that depending on the further components of the respective composition that no imparting of the own scents described herein is achieved. Thus, a skilled person may select an amount of (a) compound(s) of formula (I) advantageous for the respective application depending on the desired effect of a compound of formula (I).

A compound of formula (I) is excellently suitable for the use in a fragrance composition according to the invention due to its olfactory characteristics. A compound of formula (I) may advantageously be combined with a plurality of further fragrances and be used in a plurality of different products and articles.

Preferably it applies to a fragrance composition according to the invention that the total amount of compound(s) of formula (I) in the fragrance composition is a sensorically effective amount, preferably an amount sufficient to impart and/or enhance one or more scents selected from the group consisting of the scents green, nitrile, herbaceous, fresh, fruity, flowery, rosy, woody, sweet, earthy, fatty metallic, balsam and iris and carrot scents, preferably at least one of the scents selected from the group consisting of the scents green, nitrile, rosy and iris and carrot scents, preferably rosy with iris and carrot scents, and/or to modify one or more scents of one or, respectively, the further fragrance(s) of the fragrance composition in the direction of one or more of these scents.

It is particularly preferred if the or, respectively, one, several or all of the further fragrances (also) imparts, modifies and/or enhances one or more scents selected from the group consisting of the scents green, nitrile, herbaceous, fresh, fruity, flowery, rosy, woody, sweet, earthy, fatty, metallic, balsam and iris and carrot scents, preferably at least one of the scents selected from the group consisting of the scents woody, fruity and flowery, particularly preferably selected from the group consisting of the scents fruity and flowery. According to an alternative embodiment, the or, respectively, one, several or all of the further fragrances may impart, modify and/or enhance one or more different scents.

Examples for fragrances which may be advantageously combined with a compound of formula (I) in the scope of the present invention are e.g. found in S. Arctander, Perfume and Flavor Materials, Vol. I and II, Montclair, N. J. 1969, own publisher, or K. Bauer et al., Common Fragrance and Flavor Materials, 4th Edition, Wiley-VCH, Weinheim 2001.

Explicitly mentioned are: extracts of natural raw materials such as essential oils, concretes, absolues, resins, resinoids, balms, tinctures such as e.g. ambra tincture; amyris oil; angelica seed oil; angelica root oil; anise oil; valerian oil; basil oil; tree moss absolue; bay oil; mugwort oil; benzoe resin; bergamot oil; beeswax absolue; birch tar oil; bitter almond oil; savory oil; bucco leaf oil; cabreuva oil; cade oil; calmus oil; campher oil; cananga oil; cardamomen oil; cascarilla oil; cassia oil; cassie absolue; castoreumabsolue; cedar leaf oil; cedar wood oil; cistus oil; citronell oil; citronen oil; copaiva balm; copaiva balm oil; coriander oil; costus root oil; cumin oil; cypress oil; davana oil; dill weed oil; dill seed oil; eau de brouts absolue; oak wood absolue; elemi oil; estragon oil; eucalyptus-citriodora-oil; eucalyptus oil; fennel oil; spruce needle oil; galbanum oil; galbanum resin; geranium oil; grapefruit oil; guajak wood oil; gurjun balm; gurjun balm oil; helichrysum absolue; helichrysum oil; ginger oil; iris root absolue; iris root oil; jasmin absolue; kalmus oil; chamomile oil blau; chamomile oil roman; carrot seed oil; kaskarilla oil; pine needle oil; spearmint oil; caraway oil; labdanum oil; labdanum absolue; labdanum resin; lavandin absolue; lavandin oil; lavender absolue; lavender oil; lemongrass oil; lovage oil; lime oil distilled; lime oil pressed; linaloe oil; litsea-cubeba oil; laurel leaf oil; macis oil; majoram oil; mandarin oil; massoi bark oil; mimosa absolue; musk grain oil; musk tincture; muscatel-sage-oil; nutmeg oil; myrrh absolue; myrrh oil; myrten oil; carnation leaf oil; carnation blowwom oil; neroli oil; olibanum absolue; olibanum oil; opopanax oil; orange blossom absolue; orange oil; origanum oil; palmarosa oil; patchouli oil; perilla oil; peru balm oil; parsil leaf oil; parsil sed oil; petitgrain oil; peppermint oil; pepper oil; piment oil; pine oil; poley oil; rose absolue; rosewood oil; rose oil; rosemary oil; sage oil dalmatinic; sage oil spanish; sandalwood oil; cellerie seed oil; spica lavender oil; star anise oil; styrax oil; marigold oil; fir needle oil; tea-tree oil; turpentine oil; thyme oil; tolu balm; tonka absolue; tuberose absolue; vanilla extract; violet leaf absolue; verbena oil; vetiver oil; juniper berry oil; wine yeast oil; vermouth oil; wintergreen oil; ylang oil; ysop oil; zibet absolue; cinnamon leaf oil; cinnamon bark oil as well as fractions thereof or, respectively, ingredients isolated therefrom;

single fragrances of the group of carbohydrates such as e.g. 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrol; diphenylmethane;

of the group of aliphatic alcohols such as e.g. hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

of the group of aliphatic aldehydes and their acetals such as e.g. hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanaldiethylacetale; 1,1-dimethoxy-2,2,5-trimethyl-4-hexen; citronellyloxyacetaldehyde; 1-(1-methoxy-propoxy)-(E/Z)-3-hexene;

of the aliphatic ketones and their oximes such as e.g. 2-heptanone; 2-octanone; 3-octanone; 2-nonanone; 5-methyl-3-heptanone; 5-methyl-3-heptanonoxime; 2,4,4,7-tetramethyl-6-octen-3-one; 6-methyl-5-hepten-2-one;

of the aliphatic sulphur containing compounds such as e.g. 3-methylthio-hexanol; 3-methylthiohexyl acetate; 3-mercaptohexanol; 3-mercaptohexylacetat; 3-mercaptohexylbutyrat; 3-acetylthiohexyl acetate; 1-menthen-8-thiol;

of the aliphatic nitriles such as e.g. 2-nonenacid nitrile; 2-undecenacid nitrile; 2-tridecenacid nitrile; 3,12-tridecadienacid nitrile; 3,7-dimethyl-2,6-octadien-acid nitrile; 3,7-dimethyl-6-octenacid nitrile;

of the esters of aliphatic carboxylic acids such as e.g. (E)- and (Z)-3-hexenyl formiate; ethylaceto acetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl-isobutyrate; hexyl crotonate; ethyliso valerianate; ethyl-2-methylpentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyloxy acetate; methyl-3,7-dimethyl-2,6-octadien-oat; 4-methyl-2-pentylcrotonate;

of the acyclic terpene alcohols such as e.g. geraniol; nerol; lavadulol; nerolidol; farnesol; tetrahydrolinalool; tetrahydrogeraniol; 2,6-dimethyl-7-octen-2-ol; 2,6-dimethyloctan-2-ol; 2-methyl-6-methylen-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as their formiates, acetates, propionates, isobutyrates, butyrates, isovalerianates, pentanoates, hexanoates, crotonates, tiglinates and 3-methyl-2-butenoates;

of the acyclic terpene aldehydes and ketones such as e.g. citronellal; 7-methoxy-3,7-dimethyloctanal; 2,6,10-trimethyl-9-undecenal; geranyl acetone; as well as the dimethyl- and diethyl acetals of geranial, neral, of the cyclic terpene alcohols such as e.g. menthol; isopulegol; alpha-terpineol; terpinenol-4; menthan-8-ol; menthan-1-ol; menthan-7-ol; borneol; isoborneol; linalooloxid; nopol; cedrol; ambrinol; vetiverol; guajol; as well as their formiates, acetates, propionates, isobutyrates, butyrates, isovalerianates, pentanoates, hexanoates, crotonates, tiglinates and 3-methyl-2-butenoates;

of the cyclic terpene aldehydes and ketones such as e.g. menthone; isomenthone; 8-mercaptomenthan-3-one; carvone; campher; fenchone; alpha-ionone; beta-ionone; alphan-methylionone; beta-n-methylionone; alpha-isomethylionone; beta-isomethyl-ionone; alpha-irone; beta-damascenone; 1-(2,4,4-trimethyl-2-cyclohexen-1-yl)-2-buten-1-one; 1,3,4,6,7,8a-hexahydro-1,1,5,5-tetramethyl-2h-2,4a-methano-naphthalen-8(5h)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedar wood oil (methyl-cedrylketon);

of the cyclic alcohols such as e.g. 4-tert.-butylcyclohexanol; 3,3,5-trimethylcyclohexanol; 3-isocamphylcyclohexanol; 2,6,9-trimethyl-z2,z5,e9-cyclododecatrien-1-ol; 2-isobutyl-4-methyltetrahydro-2h-pyran-4-ol;

of the cycloaliphatic alcohols such as e.g. alpha,3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

of the cyclic and cycloaliphatic ethers such as e.g. cineol; cedrylmethylether; cyclododecylmethylether; 1,1-dimethoxycyclododecan; (ethoxymethoxy)cyclo-dodecan; alphacedrenepoxid; 3a,6,6,9a-tetramethyldodecahydronaphtho[2,1-b]furan; 3a-ethyl-6,6,9 a-trimethyldodecahydronaphtho[2,1b]furan; 1,5,9-tri-methyl-13-oxabicyclo[10.1.0]trideca-4,8-dien; rosenoxide; 2-(2,4-dimethyl-3-cyclohexen-1-yl)-5-methyl-5-(1-methylpropyl)-1,3-dioxan;

of the cyclic and macrocyclic ketones such as e.g. 4-tert.butylcyclohexanone; 2,2,5-trimethyl-5-pentylcyclopentanone; 2-heptylcyclopentanone; 2-pentyl-cyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopenta-decanone; 4-(1-ethoxyvinyl)-3,3,5,5-tetramethylcyclohexanone; 4-tert.-pentylcyclo-hexanone; 5-cyclohexadecen-1-one; 6,7-dihydro-1,1,2,3,3-pentamethyl-4(5h)-indanone; 8-cyclohexadecen-1-one; 9-cycloheptadecen-1-one; cyclopentadecanone; cyclohexadecanone;

of the cycloaliphatic aldehydes such as e.g. 2-methyl-4-(2,2,6-trimethyl-cyclohexen-1-yl)-2-butenal; 4-(4-hydroxy-4-methylpentyl)-3-cyclohexencarbaldehyde; 4-(4-methyl-3-penten-1-yl)-3-cyclohexencarbaldehyde;

of the cycloaliphatic ketones such as e.g. 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphtalenylmethylketone; methyl-2,6,10-trimethyl-2,5,9-cyclododecatrienylketone; tert.butyl-(2,4-dimethyl-3-cyclohexen-1-yl)ketone;

of the esters of cyclic alcohols such as e.g. 2-tert-butylcyclohexyl acetate; 4-tert-butylcyclohexyl acetate; 2-tert-pentylcyclohexyl acetate; 4-tert-pentyl-cyclo-hexyl-acetate; 3,3,5-trimethylcyclohexyl acetate; decahydro-2-naphthyl acetate; 2-cyclopentylcyclopentylcrotonat; 3-pentyltetrahydro-2h-pyran-4-yl acetate; decahydro-2,5,5,8a-tetramethyl-2-naphthyl acetate; 4,7-methano-3a,4,5,6,7,7a-hexahydro-5, or, respectively, 6-indenyl acetate; 4,7-methano-3a,4,5,6,7,7a-hexahydro-5, or, respectively, 6-indenyl propionate; 4,7-methano-3a,4,5,6,7,7a-hexahydro-5, or, respectively, 6-inden-yl isobutyrate; 4,7-methanooctahydro-5, or, respectively 6-indenyl acetate;

of the esters of cycloaliphatic alcohols such as e.g. 1-cyclohexylethyl crotonate;

of the esters of cycloaliphatic carboxylic acids such as e.g. allyl-3-cyclohexyl propionate; allylcyclohexyloxy acetate; cis- and trans-methyldihydro jasmonate; cis- and trans-methyl jasmonate; methyl-2-hexyl-3-oxocyclopentan carboxylate; ethyl-2-ethyl-6,6-dimethyl-2-cyclohexen carboxylate; ethyl-2,3,6,6-tetramethyl-2-cyclohexen carboxylate; ethyl-2-methyl-1,3-dioxolan-2-acetate;

of the araliphatic alcohols such as e.g. benzyl alcohol; 1-phenylethyl alcohol; 3-phenyl propanol; 2-phenyl propanol; 2-phenoxy ethanol; 2,2-dimethyl-3-phenyl propanol; 2,2-dimethyl-3-(3-methylphenyl) propanol; 1,1-dimethyl-2-phenylethyl alcohol; 1,1-dimethyl-3-phenyl propanol; 1-ethyl-1-methyl-3-phenyl propanol; 2-methyl-5-phenyl pentanol; 3-methyl-5-phenyl pentanol; 3-phenyl-2-propen-1-ol; 4-methoxybenzyl alcohol; 1-(4-isopropylphenyl) ethanol;

of the esters of araliphatic alcohols and aliphatic carboxylic acids such as e.g. benzyl acetate; benzyl propionate; benzyl isobutyrate; benzyl isovalerianate; 2-phenylethyl acetate; 2-phenylethyl propionate; 2-phenylethyl isobutyrate; 2-phenyl-ethyl isovalerianate; 1-phenylethyl acetate; alpha-trichlormethylbenzyl acetate; alpha, alpha-dimethylphenyl-ethyl acetate; alpha,alpha-dimethylphenylethyl butyrate; cinnamyl acetate; 2-phenoxyethyl isobutyrate; 4-methoxybenzyl acetate;

of the araliphatic ethers such as e.g. 2-phenylethylmethyl ether; 2-phenylethyl-isoamyl ether; 2-phenylethyl-1-ethoxyethyl ether; phenylacetaldehyddimethyl acetal; phenylacetaldehyddiethyl acetal; hydratropaaldehyddimethyl acetal; phenylacetaldehydglycerin acetal; 2,4,6-trimethyl-4-phenyl-1,3-dioxan; 4,4a,5,9b-tetra-hydroindeno[1,2-d]-m-dioxin; 4,4a,5,9b-tetrahydro-2,4-dimethylindeno[1,2-d]-m-dioxin;

of the aromatic and araliphatic aldehydes such as e.g. benzaldehyde; phenyl acetaldehyde; 3-phenyl propanal; hydratropa aldehyde; 4-methyl benzaldehyde; 4-methylphenyl acetaldehyde; 3-(4-ethylphenyl)-2,2-dimethyl propanal; 2-methyl-3-(4-isopropylphenyl) propanal; 2-methyl-3-(4-isobutylphenyl) propanal; 3-(4-tert.-butyl-phenyl) propanal; cinnamic aldehyde; alpha-butylcinnamic aldehyde; alpha-hexylcinnamic aldehyde; 3-methyl-5-phenyl pentanal; 4-methoxy benzaldehyde; 4-hydroxy-3-methoxy benzaldehyde; 4-hydroxy-3-ethoxy benzaldehyde; 3,4-methylendioxy benzaldehyde; 3,4-dimethoxy benzaldehyde; 2-methyl-3-(4-methoxyphenyl) propanal; 2-methyl-3-(4-methylendioxyphenyl) propanal;

of the aromatic and araliphatic ketones such as e.g. acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphtha-lenyl) ethanone; 2-benzofuranyl ethanone; (3-methyl-2-benzofuranyl) ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1h-5-indenyl] ethanone; 5',6',7',8'-tetrahydro-3',5',5',6',8',8'-hexamethyl-2-acetonaphthone;

of the aromatic and araliphatic carboxylic acids and their esters such as e.g. benzoic acid; phenyl acetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allylphenoxy acetate; methyl salicylate; hexyl salicylate; cyclohexyl salicylate; cis-3-hexenyl salicylate; benzyl salicylate; phenylethyl salicylate; methyl-2,4-dihydroxy-3,6-dimethyl benzoate; ethyl-3-phenyl glycidate; ethyl-3-methyl-3-phenyl glycidate;

of the nitrogen containing aromatic compounds such as e.g. 2,4,6-trinitro-1,3-dimethyl-5-tert.-butylbenzol; 3,5-dinitro-2,6-dimethyl-4-tert.-butyl acetophenone; cinnamic acid nitrile; 3-methyl-5-phenyl-2-pentenic acid nitrile; 3-methyl-5-phenyl valeric acid nitrile; methyl anthranilate; methy-n-methyl anthranilate; schiff bases of methyl anthranilate with 7-hydroxy-3,7-dimethyl octanal, 2-methyl-3-(4-tert.-butylphenyl) propanal or 2,4-dimethyl-3-cyclohexene carbaldehyde; 6-isopropyl chinolin; 6-isobutyl chinolin; 6-sec.-butyl chinolin; 2-(3-phenylpropyl) pyridine; indol; skatol; 2-methoxy-3-isopropyl pyrazin; 2-isobutyl-3-methoxy pyrazin;

of the phenols, phenyl ethers and phenyl esters such as e.g. estragol; anethol; eugenylmethyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxy benzol; eugenyl acetate; 2-methoxy-4-methyl phenol; 2-ethoxy-5-(1-propenyl) phenol; p-cresyl phenyl acetate;

of the heterocyclic compounds such as e.g. 2,5-dimethyl-4-hydroxy-2h-furan-3-one; 2-ethyl-4-hydroxy-5-methyl-2h-furan-3-one; 3-hydroxy-2-methyl-4h-pyran-4-one; 2-ethyl-3-hydroxy-4h-pyran-4-one;

of the lactones such as e.g. 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadeca-nolide; 9-hexadecen-1,16-olide; 10-oxa-1,16-hexadecanolide; 11-oxa-1,16-hexa-decanolide; 12-oxa-1,16-hexadecanolide; ethylen-1,12-dodecandioat; ethylen-1,13-tridecandioat; 2,3-dihydrocumarin; octahydro cumarin.

Particularly preferred are such fragrances which impart a flowery and/or fruity scent. Partiularly for such fragrances, an olfactory enhancement of the flowery and/or fruity scent is advantageously (at least partially) achieved by a compound of formula (I) to be used according to the present invention.

Flowery fragrances which may particularly advantageously be combined with the compounds of formula (I) to be used according to the present invention (particularly in fragrance compositions according to the invention) are preferably selected from the group consisting of hydroxy citronellal, methoxy citronellal, cyclamen aldehyde [2-methyl-3-(4-isopropylphenyl) propanal], 1-(4-isopropyl-cyclohexyl) ethanol (Mugetanol®), 4-tert.-butyl-α-methyldihydro cinnamic aldehyde (Lilia®), cis-hexahydrocuminyl alcohol (Mayol®), 3-[4-(1,1-dimethylethyl)phenyl]propanal (Bourgeonal®), 2,2-dimethyl-3-(3-methylphenyl) propanol (Majantol®), 3-methyl-3-(3-methylbenzyl)-butan-2-ol, 2-isobutyl-4-methyltetrahydro-2h-pyran-4-ol (Florosa®), 2-methyl-3-(3,4-methylendioxyphenyl) propanal (Heliofolal®), 4-(4-hydroxy-4-methylpentyl)-3-cyclohexen carbaldehyde (Lyral®), 4-(octahydro-4,7-methano-5h-inden-5-yliden butanal (Dupical®), vernaldehyde, 4-(4-methyl-3-penten-1-yl)-3-cyclohexencarb aldehyde (Vertomugal®), octahydro-5-(4-methoxybutyliden)-4,7-methano-1h-inden (Mugoflor®), 2,6-dimethyl-2-heptanol (Freesiol®), 1-ethyl-1-methyl-3-phenyl propanol (Phemec®), 2,2-dimethyl-3-phenyl-1-propanol (muguet alcohol), profarnesol, dihydrofarnesol, farnesol, nerolidol, hydroxycitronellaldimethyl acetal, hexyl benzoate, geraniol, nerol, linalool, tetrahydrogeraniol, tetrahydrolinalool, ethyllinalool, geranyltiglinat, phenethylalcohol (2-phenylethylalcohol), citronellol, rosenoxide, 2-methyl-5-phenylpentanol (rosaphen), 3-methyl-5-phenyl pentanol (phenoxanol), methyldihydro jasmonate (Hedion®, Hedione® high cis), 2-heptyl-cyclopentanon (projasmon p), cisjasmon, dihydrojasmon, cinnamic alcohol (3-phenyl-2-propen-1-ol), dihydrocinnamic alcohol (3-phenylpropanol), 2-methyl-4-phenyl-1,3-dioxolan (Jacinthaflor®) and dihydromyrcenol (2,6-dimethyl-7-octen-2-ol).

Fruity fragrances with which compounds of formula (i) to be used according to the invention may advantageously be combined and which thereafter are particularly preferred (further) fragrances of a fragrance composition according to the invention are preferably selected from the group consisting of: 2-methyl-butyric acid ethyl ester, 4-(p-hydroxyphenyl)-2-butanone, ethyl-3-methyl-3-phenylglycidate, butyric acid isoamyl ester, acetic acid isoamyl ester, acetic acid-n-butyl ester, butyric acid ethyl ester, 3-methyl-butyric acid ethyl ester, n-hexanoic acid ethxyl ester, n-hexanoic acid allyl ester, ethyl-2-trans-4-cis-decadienoat, 1,1-dimethoxy-2,2,5-trimethyl-4-hexan, 2,6-dimethyl-5-hepten-1-al, gamma-undecalactone, gamma-nonalactone, hexanal, 3z-hexenal, n-decanal, n-dodecanal, citral, vanillin, ethylvanillin, maltol, ethylmaltol and their mixtures.

Fragrance compositions according to the invention which contain a compound of formula (I) can be/become present as liquid form, undiluted or diluted with a solvent and be advantageously used for perfuming. Preferred solvents in this context are Ethanol, Isopropanol, diethylene glycol monoethyl ether, glycerin, propylene glycol, 1,2-butylene glycol, dipropylene glycol, diethylphtalate, triethyl citrate, isopropyl myristate, triacetin and diacetin.

Furthermore, fragrance compositions according to the invention may be adsorbed to a carrier which provides a fine distribution of the fragrances in a product as well as for a controlled release during the application. Such carriers may be porous inorganic materials such as light sulfates, silica gels, zeolites, gypsum, clays, clay granules, aerated concrete and the like or organic materials such as woods, cellulose based substances, sugars, dextrins (e.g. maltodextrin) or synthetic materials such as PVC, polyvinyl acetates or polyurethanes. The resulting combination of composition according to the invention and carrier is also considered as fragrance composition according to the invention or can be present as product according to the invention (as described herein below).

Fragrance composition or products (as described herein below) according to the invention may also be present as microencapsuled, spray dried, as inclusion-complexes or as extrusion products and—in case of a fragrance composition—be added e.g. to a product to be perfumed (as described herein below) in this form.

Where applicable, the characteristics of such modified compositions or products may further be optimized by so-called coating with suitable materials with regard to a more targeted fragrance release, wherein preferably waxy synthetic materials such as e.g. polyvinyl alcohol are used. The resulting products are in turn considered as products according to the invention.

A microencapsulation may e.g. be performed by the so-called coacervation method using capsule materials e.g. of polyurethane containing substances or soft gelatin.

Spray dried products are preferably produced by spray drying of an emulsion or, respectively, dispersion containing the fragrance composition, wherein as carriers modified starches, proteins, dextrin and vegetable gums may be used.

Inclusion-complexes may e.g. be produced by applying dispersions of the fragrance composition and cyclodextrins or urea derivatives in a suitable solvent e.g. water.

Extrusion products can be obtained e.g. by melting the fragrance compositions with a suitable waxy substance and by extrusion with subsequent solidification, where applicable in a suitable solvent e.g. isopropanol.

A further aspect of the present invention relates to the use of a fragrance composition according to the invention for imparting, modifying and/or enhancing of one or more scents selected from the group consisting of the scents green, nitrile herbaceous, fresh, fruity, flowery, rosy, woody, sweet, earthy, fatty, metallic, balm and iris and carrot scents, preferably at least one of the scents selected from the group consisting of the scents green, nitrile, rosy and iris and carrot scents, preferably rosy with iris and carrot scents.

What was said above in connection with a use according to the invention or with fragrance compositions according to the invention applies accordingly for preferred embodiments herein.

Fragrance compositions according to the invention can advantageously be present in concentrated form, in solutions or in modified form as described above, for the production of perfumed products according to the invention, e.g. perfume extraits, eau de parfums, eau de toilettes, aftershaves, eau de colognes, pre-shave-products, splash-colognes and perfumed refreshing tissues, as well as for the perfuming of acid, alkaline and neutral cleaning agents such as e.g. floor cleaners, window glass cleaners, dishwashing detergents, bathroom and sanitary cleaners, scouring agents, solid and liquid toilet cleaners, carpet cleaning agents in powder and foam form, textile refreshing agents, ironing aids, liquid washing agents, washing agents in powder form, laundry pre-treatment agents such as bleaching agents, soaking agents and stain removers, fabric softeners, laundry soap, laundry tablets, disinfectants, surface disinfectants as well as of air refreshers in liquid or gel-like form or mounted on a carrier, aerosols, waxes and polishes such as furniture polish, floor waxes, shoe polish as well as body care agents such as e.g. solid and liquid soaps, shower gels, shampoos, shaving soaps, shaving foams, bath oils, cosmetic emulsions of the oil-in-water, water-in-oil and of the water-in-oil-in-water type such as e.g. body lotions, face lotions, sun protectors and sun lotions, after-sun lotions, hand lotions, foot lotions, depilatory creams and lotions, aftershave creams and lotions, tanning creams and lotions, hair-care products such as e.g. hair sprays, hair gels, solidifying hair lotions, conditioners, permanent and semipermanent hair dying agents, hair forming agents such as cold wave and hair smoothing agents, hair waters, hair lotions, deodorants, anti-transpirants such as e.g. armpit sprays, roll-ons, deodorant sticks, deodorant creams, products of decorative cosmetics such as e.g. eyeshadow, nail varnish, make-ups, lip sticks, mascara as well as of candles, lamp oils, joss sticks, insecticides, repellents and propellants.

A further aspect of the present invention thus relates to a perfumed product comprising or consisting of
(i) a fragrance composition according to the invention (as described herein),
or
one or more compound(s) of formula (I)

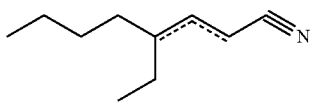

(I)

and one, two, three, four, five, six, seven, eight, nine, ten or more further fragrance(s), wherein the weight ratio of the total amount of compound(s) of formula (I) to the total amount of further fragrance(s) is in a range of from 1:1000 to 1:0.1, preferably of from 1:1000 to 1:0.5,
and
(ii) one or more further component(s), preferably at least one or more, preferably one, two, three, four, five or more additive(s), excipient(s) and/or active substance(s).

What was said above in connection with a use according to the invention of with fragrance compositions according to the invention applies accordingly for preferred embodiments herein.

Preferably, a product according to the invention is selected from the group consisting of washing and cleaning agents, hygiene or care products, preferably in the field of body and hair care, cosmetics and home care, preferably selected from the group consisting of perfume extraits, eau de parfums, eau de toilettes, aftershaves, eau de colognes, preshave-products, splash-colognes, perfumed refreshing tissues, acid, alkaline or neutral cleaning agents, textile refreshing agents, ironing aids, liquid washing agents, washing agents in powder form, laundry pre-treatment agents, fabric softeners, laundry soap, laundry tablets, disinfectants, surface disinfectants, air refreshers, aerosols, waxes and polishes, body care agents, hand creams and lotions, foot creams and lotions, depilatory creams and lotions, aftershave creams and lotions, tanning creams and lotions, hair-care products deodorants, anti-perspirants, products of decorative cosmetics, candles, lamp oils, joss sticks, insecticides, repellents and propellants.

It preferably also applies to a perfumed product according to the invention that component (i) is present in a sensorically effective amount, preferably in an amount sufficient for that a consumer perceives one or more scents selected from the group consisting of the scents green, nitrile, herbaceous, fresh, fruity, flowery, rosy, woody, sweet, earthy, fatty, metallic, balm and iris and carrot scents, preferably at least one of the scents selected from the group consisting of the scents green, nitrile, rosy and iris and carrot scents, preferably rosy with iris and carrot scents.

It is also preferred that the perfumed product contains a total amount of compound(s) of formula (I), related to the total weight of the product in a range of from 0.00001 to 10 wt.-%, preferably 0.0001 to 5 wt.-%, particularly preferably 0.001 to 2 wt.-%, further preferably 0.005 to 1 wt.-%.

The additives, excipients and/or active substances are preferably no fragrances and are, if present, preferably selected from the group consisting of:

Preservatives, preferably those mentioned in US 2006/0089413, abrasives, anti-acne agents and agents for the reduction of sebum, preferably those mentioned in WO 2008/046791, agents against skin aging, preferably those mentioned in WO 2005/123101, anti-bacterial agents, anti-cellulitis agents, anti-dandruff agents, preferably those mentioned in WO 2008/046795, anti-inflammatory agents, irritation preventing agents, anti-irritants (anti-inflammatory, irritation inhibiting and irritation preventing agents), preferably those mentioned in WO 2007/042472 and US 2006/0089413, antimicrobial agents, preferably those mentioned in WO 2005/123101, anti-oxidants, preferably those mentioned in WO 2005/123101, astringents, antiseptic agents, antistatics, binders, buffers, carriers, preferably those mentioned in WO 2005/123101, cell stimulants, cleaning agents, caring agents, depilatory agents, surface active substances, deodorizing agents and anti-perspirants, preferably those mentioned in WO 2005/123101, softeners, emulsifiers, preferably those mentioned in WO 2005/123101, enzymes, essential oils, preferably those mentioned in US 2008/0070825, insect repellents, preferably those selected in WO 2005/123101, fibers, film formers, (further) fixators, foam formers, foam stabilizers, substances for preventing foaming, foam boosters, fungicides, gelling agents and gel forming agents, preferably those mentioned in WO 2005/123101, hair care agents, hair forming agents, hair smoothing agents, moisture regulators (moisturizers, moistening agents and/or humectants), preferably those mentioned in WO 2005/123101, compatible solutes, preferably those mentioned in WO 01/76572 and WO 02/15686, bleaching agents, strengthening agents, stain removing agents, optically bleaching agents, impregnating agents, stain-resistant agents, friction reducing agents, lubricants, moisturizing creams, ointments, opacifiers, plasticising agents, opaque agents, polish, brighteners, polymers, preferably those mentioned in WO 2005/123101 and WO 2008/046676, re-fattening agents, grinding agents, skin calming agents, skin cleaning agents, skin caring agents, skin healing agents (skin repair agents), preferably containing cholesterol and/or fatty acids and/or ceramides and/or phseudoceramides, preferably those mentioned in WO 2006/053912, skin whiteners, preferably those mentioned in WO 2007/110415, skin protecting agents, skin softening agents, skin cooling agents, preferably those mentioned in WO 2005/123101, skin warming agents, preferably those mentioned in WO 2005/123101, stabilizers, UV-absorbing agents and UV-filters, preferably those mentioned in WO 2005/123101,beznylidene-beta-dicarbonyl compounds preferably those mentioned in WO 2005/107692, alpha-benzoyl cinnamic cid nitriles, preferably those mentioned in WO 2006/015954, AhR-receptor antagonists, preferably those mentioned in WO 2007/128723 and WO 2007/060256, washing agents, fabric softeners, suspending agents, skin tanning agents, preferably those mentioned in WO 2006/045760, t thickeners, vitamins, preferably those mentioned in WO 2005/123101, fat oils, waxes and fats, preferably those mentioned in WO 2005/123101, phospholipids, preferably those mentioned in WO 2005/123101, fatty acids (saturated fatty acids, single or multiple unsaturated fatty acids, α-hydroxy acids, polyhydroxy fatty acids), preferably those mentioned in WO 2005/123101, dyes and colour protecting agents as well as pigments, preferably those mentioned in WO 2005/123101, anti-corrosives, alcohols and polyols, preferably those mentioned in WO 2005/123101, surfactants, preferably those mentioned in WO 2005/123101, animal extracts, yeast extracts, extracts from algae or microalgae, electrolytes, condensers, organic solvents, preferably those mentioned in WO 2005/123101, agents modulating hair growth (promoting or inhibiting hair growth), preferably those mentioned in EP 2168570 and EP 2193785, or silicones and silicone derivatives, preferably those mentioned in WO 2008/046676,
preferably selected from the group consisting of preservatives, inorganic salts, chelate formers, detergents, skin and/or hair care agents, enzymes, emulsifiers, fats, fat oils, waxes, fat alcohols, silicones, silicone derivatives and water.

A further aspect of the present invention relates to a method for perfuming a product (for preferred products, cf. above), comprising or consisting of the following steps:
(a) providing
(a.1) a fragrance composition according to the invention (as described herein),
or
(a.2) one or more compound(s) of formula (I)

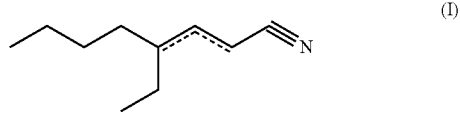

and optionally one, two, three, four, five, six, seven, eight, nine, ten or more further fragrance(s), wherein the weight ratio of the total amount of compound(s) of formula (I) to the total amount of further fragrance(s) is in a range of from 1:1000 to 1:0.1, preferably of from 1:1000 to 1:0.5,
and
(b) adding the fragrance composition (a.1) or, respectively, compound(s)/fragrance(s) (a.2) to the product to be perfumed in a sensorically effective amount, preferably in an amount sufficient to impart, enhance and/or modify one or more scents selected from the group consisting of the scents green, nitrile, herbaceous, fresh, fruity, flowery, rosy, woody, sweet, earthy, fatty, metallic, balm and iris and carrot scents, preferably at least one of the scents selected from the group consisting of the scents green, nitrile, rosy and iris and carrot scents, preferably rosy with iris and carrot scents.

The present invention further relates to a method for perfuming hair, skin, textile fibers, surfaces and/or room air comprising or consisting of the following steps:
(a) providing
(a.1) a fragrance composition according to the invention (as described herein), preferably containing a surfactant or a surfactant mixture,
or
(a.2) one or more compound(s) of formula (I)

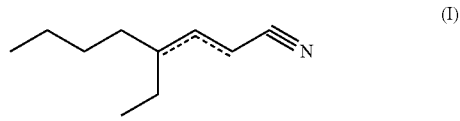

and optionally one, two, three, four, five, six, seven, eight, nine, ten or more further fragrance(s), wherein the weight ratio of the total amount of compound(s) of formula (I) to the total amount of further fragrance(s) is in a range of from 1:1000 to 1:0.1, preferably of from 1:1000 to 1:0.5,
and additionally preferably a surfactant or a surfactant mixture,
or
(a.3) a product according to the invention (as described herein) preferably containing a surfactant or a surfactant mixture
and
(b) adding the fragrance composition (a.1) or, respectively, the compound(s)/fragrance(s) (a.2) or, respectively, the product (a.3) to the hair or, respectively, skin or, respectively, fibers or, respectively, surface or, respectively, in the room air to be perfumed in a sensorically effective amount, preferably in an amount sufficient for that a consumer perceives one or more scents selected from the group consisting of the scents green, nitrile, herbaceous, fresh, fruity, flowery, rosy, woody, sweet, earthy, fatty, metallic, balm and iris and carrot scents, preferably at least one of the scents selected from the group consisting of the scents green, nitrile, rosy and iris and carrot scents, preferably rosy with iris and carrot scents.

What was said above in connection with a use according to the invention of with fragrance compositions according to the invention or with a product according to the invention applies accordingly for preferred embodiments herein.

Subsequently, the invention is further explained by selected examples. If not stated otherwise, all indications refer to the weight.

Abbreviations: DPG=Dipropylene glycol, TEC=Triethyl citrate

EXAMPLE 1: PRODUCTION OF 4-ETHYL-OCTEN-2/3-NITRILE 254 g of 2-ethyl hexanal, 38 g of ammonium acetate and 46 g acetic acid were provided in 520 g toluene in a 1000 ml agitator with water separator. Subsequently, 189 g cyano acetic acid were added at room temperature in portions and while stirring. Thereafter, it was refluxed for 14 h at the water separator and washed with 10% sulphuric acid, 5% sodium hydroxide or, respectively, water after cooling. The organic phase was reduced and the raw product (280 g) was fractionated distilled at a 40 cm vigreux-column in vacuum.

Yield: 190 g (63.9% of theory) boiling point: 80°-85° C./0.8 mbar

GC-analysis (20m DB-WAX, inner diameter 0.18 μm/60-9-220° C. programmed temperature vaporising injector)

The product consists of 4 isomers, 4.5% (E/Z) 4-ethyl-octen-2-nitrile and 95.5% (E/Z) 4-ethyl-octen-3-nitrile.

(E/Z) 4-ethyl-octen-2-nitrile

MS: m/z (%)=150(2), 136(7), 122(14), 110(38), 97(54), 80(100), 70(48), 55(78), 41(89)

MS: m/z (%)=150(2), 136(5), 122(12), 110(27), 97(51), 80(67), 70(65), 56(100), 41(94) (E/Z) 4-ethyl-octen-3-nitrile MS: m/z (%)=151(2), 136(2), 122(4), 110(26), 94(32), 81(23), 69(100), 55(21), 41(43)

MS: m/z (%)=151(2), 136(2), 122(5), 110(25), 94(32), 81(22), 69(100), 55(21), 41(42)

EXAMPLE 1A: PRODUCTION OF 4-ETHYL-OCTEN-2/3-NITRILE 254 g of 2-ethyl hexanal and 189 g of cyano acetic acid were provided in 500 ml cyclohexane in a 1000 ml agitator with water separator and dropping funnel. Afterwards, 65 g of 3-picolin were added while stirring and boiling. Subsequently, it was refluxed for 26 h at the water separator and washed with 10% sulphuric acid, 5% sodium hydroxide or, respectively, water after cooling. The organic phase was reduced and the raw product (250 g) was obtained. The raw product consists of 4 isomers, 16.5% (E/Z) 4-ethyl-octen-2-nitrile and 63.9% (E/Z) 4-ethyl-octen-3-nitrile.

The raw product is fractionated distilled at a canned-column in vacuum.

Yield of the product: 37.5 g (E/Z) 4-ethyl-octen-2-nitrile (95.4%)

Boiling point.: 75°-80° C./0.8 mbar

GC-analysis (20 m DB-WAX, inner diameter 0.18 μm/60-9-220° C. programmed temperature vaporising injector)

EXAMPLE 2: PERFUME COMPOSITION (FRAGRANCE COMPOSITION)

| | |
|---|---|
| AMAROCIT ® 10% DPG | 6 |
| AMBRETTOLIDE | 2 |
| AMBRINOL S 10% DPG | 6 |
| BENZOIN OLIFFAC TYPE BASE | 8 |
| CASSIS 345B TYPE BASE W/O MYRCENE | 10 |
| DECALACTON DELTA 10% DPG | 3 |
| DIHYDROIONON BETA | 6 |
| DIHYDROJASMON 10% DPG | 3.5 |
| DIHYDROMYRCENOL | 6 |
| DIPROPYLENE GLYCOL | 63 |
| EBANOL 10% DPG | 6 |
| ETHYLENE BRASSYLAT | 80 |
| ETHYLLINALOOL | 10 |
| ETHYLMALTOL 10% DPG | 1 |
| FLOROSA BM/PYRANOL | 5 |
| GLOBALIDE ® | 18 |
| GLOBANONE ® | 12 |
| HEDION | 140 |
| HELIONAL | 10 |
| HELIOTROPIN/PIPERONAL | 3 |
| HEXYL ACETATE | 3 |
| IONON ALPHA | 30 |
| IRISNITRIL 1% DPG | 4 |
| IRON ALPHA 10% DPG | 3 |
| ISO E SUPER | 80 |
| KOAVONE | 6 |
| LACTOJASMONE | 1 |
| MACROLIDE ® SUPRA | 10 |
| MENTHANYL ACETATE | 10 |
| METHYLHEPTENON-6,5,2 10% DPG | 2 |
| MUSCENONE | 1 |
| MYSORE ACETAT | 15 |
| OCTAHYDROCUMARIN | 1.5 |
| ORANGENOEL 5X | 1 |
| PENTYL ACETATE N 1% DPG | 10 |
| PHENOXANOL | 25 |
| SANDALORE | 15 |
| SANDRANOL ® | 20 |
| TERPINYLACETAT | 20 |
| TETRAHYDROLINALOOL | 30 |
| VANILLIN | 8 |
| YSAMBER ® K | 6 |
| DIPROPYLENE GLYCOL | 300 |

According to the perfumers, this perfume composition becomes more dry, powdery, complemented and harmonic by the addition of 0.5 wt.-% of a compound of formula (Ia) or (Ib) or, respectively, a mixture of (Ia) and (Ib), wherein a clear iris-violet and rose scent occurs and the woody and flowery aspects are enhanced. The combination or, respectively, use according to the invention provides an own character to the composition and connects the different olfactory elements.

EXAMPLE 3: PERFUME COMPOSITION (FRAGRANCE COMPOSITION)

| | |
|---|---|
| AMBERWOOD ® F | 30 |
| AMBRA CORE | 70 |
| AMBROCENIDE ® 10 DPG 10% DPG | 10 |
| AMBROXIDE | 10 |
| AMYLSALICYLATE N | 3 |
| BERGAMOTT ECO ESSENCE | 15 |
| CARDAMOMENOEL GUATEMALA | 2 |
| CEDAR WOOD OIL VIRGINIA | 10 |
| CHOCOLAT NOIR 0.1% DPG | 10 |
| CUMARIN | 10 |
| DAMASCENON 10% DPG | 5 |
| DIPROPYLENE GLYCOL | 449 |
| GLOBALIDE ® | 100 |
| HEDION | 20 |
| HELIOTROPIN/PIPERONAL | 3 |
| HEXENYLSALICYLATE CIS-3 | 8 |
| IONON BETA | 3 |
| ISO E SUPER NON DISCOLORING | 200 |
| LINALOOL | 5 |
| RED BERRIES EXTRACT | 2 |
| SANDALORE | 5 |
| SANDRANOL ® | 2 |
| TIMBEROL ® | 10 |
| VANILLIN | 10 |
| DIPROPYLENE GLYCOL | 8 |

According to the perfumers, this perfume composition arises by the addition of 2 wt.-% of a compound of formula (Ia) or (Ib) or, respectively, a mixture of (Ia) and (Ib) 10% in DPG. The impression of floweriness is enhanced. The composition appears more woody, more complemented and more harmonic, wherein an authentic scent occurs.

EXAMPLE 4: PERFUME COMPOSITION (FRAGRANCE COMPOSITION)

| | |
|---|---|
| ACETYL PYRAZINE-2/1% IN TEC 1% DPG | 4 |
| AMBROXIDE | 15 |
| BOISIRIS | 60 |
| CEDRENE | 5 |
| CETONE ALPHA | 5 |
| DIPROPYLENE GLYCOL | 25 |
| ETHYLVANILLIN 10% DPG | 5 |
| GLOBALIDE ® | 45 |
| HEDION HC/70 | 300 |
| IONON BETA | 15 |
| IONON BETA NAT. | 15 |
| IRISNITRIL 0.1% DPG | 20 |
| ISO E SUPER | 100 |
| ISORALDEIN 70 | 35 |
| LAIT CHAUD | 1 |
| NEROLIDOL | 30 |
| NONENAL TRANS-2 0.1% DPG | 5 |
| VELVIONE | 15 |

According to the perfumers, this perfume composition improves by the addition of 5 wt.-% of a compound of formula (Ia) or (Ib) or, respectively, a mixture of (Ia) and (Ib) 1% in DPG. The flowery impression is enhanced. The composition appears more woody, more complemented and more harmonic, wherein an authentic scent occurs.

EXAMPLE 5: SHAMPOO

The product to be used according to the invention of Example 1 or, respectively, 1a was added in a dose of 0.5 wt.-% to a shampoo base with the following composition:

| | |
|---|---|
| Sodium laurylether sulfate | 12% |
| (e.g. Texapon NSO, Fa. Cognis Deutschland GmbH) | |
| Cocamidopropylbetain | 2% |
| (z.B. Dehyton K, Fa. Cognis Deutschland GmbH) | |
| Sodium chloride | 1.4% |
| Citric acid | 1.3% |
| Phenoxyethanol, methyl-, ethyl-, butyl-, and propyl parabene | 0.5% |
| Water | 82.8% |

The pH value of the shampoo base was approximately 6. 100 mL of a 20 wt.-% aqueous shampoo solution were obtained therefrom. In this shampoo solution, 2 hair strands were washed together for 2 minutes and subsequently rinsed for 20 seconds at running lukewarm water. One hair strand was wrapped wet in aluminium foil and the second strand was dried with a hair dryer. Both hair strains were evaluated for their smell by a panel.

The description of the odour of both hair strains was as follows: strongly green, nitrile, rosy with iris and carrot scents.

EXAMPLE 6: CONDITIONER

The perfume composition of Example 2 was (after addition of 0.5 wt.-% of the product of Example 1 or, respectively, 1a) added in a dose of 0.5 wt.-% in a conditioner base with the following composition:

| | |
|---|---|
| Quarternary Ammonium methosulfate (Esterquat), approx. 90% | 5.5% |
| (e.g. Rewoquat WE 18, Witco Surfactants GmbH) | |
| Alkyl dimethyl benzyl ammonium chloride, approx. 50% | 0.2% |
| (e.g. Preventol R50, Bayer AG) | |
| Dye solution, approx. 1% | 0.3% |
| Water | 94.0% |

The pH value of the conditioner base was in a range of 2 to 3. Two cloth rags were rinsed with 370 g of a 1% aqueous conditioner solution based on the conditioner base comprising 0.5 wt.-% of the perfume composition of Example 2 in a linetest machine in the conditioner programme for 30 minutes at 20° C. The rags were sealed wet and hung for drying. Subsequently, both rags were evaluated for their smell by a panel.

The description of the odour of both cloth rags was as follows: more dry, more powdery, more complemented and more harmonic with a clear iris-violet and rose scent.

EXAMPLE 7: WASHING POWDER

The perfume oil composition of Example 3 was (after addition of 0.5 wt.-% of the product of Example 1 or, respectively, 1a 10% in DPG) added in a dose of 0.4 wt.-% in a washing powder base of the following composition:

| | |
|---|---|
| Linear Na-Alkylbenzol sulfonate | 8.8% |
| Ethoxylated Fat alcohol C12-18 (7 EO) | 4.7% |
| Na-Soap | 3.2% |
| Defoamer DOW CORNING 2-4248S | 3.9% |
| POWDERED ANTIFOAM, silicone oil on zeolith as carrier | |
| Zeolith 4A | 28.3% |
| Na-carbonate | 11.6% |
| Na-Salt of a co-polymer of acryl and maleic acid | 2.4% |
| (Sokalan CP5) | |
| Na-silicate | 3.0% |
| Carboxymethyl cellulose | 1.2% |
| Dequest 2066 | 2.8% |
| ([[(Phosphonomethyl)imino]bis[(ethylennitrilo)bis (methylen)]]tetrakis-phosphonic acid, sodium salt) | |
| Optical brightener | 0.2% |
| Na-sulfate | 6.5% |
| Protease | 0.4% |
| Sodium perborate-tetrahydrate | 22.0% |
| TAED | 1.0% |

Two cloth rags were washed with 370 g of a 1% aqueous washing powder brine based on the washing powder base comprising 0.4 wt.-% of the perfume oil composition of Example 3 (the pH value of the washing powder brine is clearly in the alkaline range) in a linetest machine in the main washing programme for 45 minutes at 60° C. The rags were first washed for 5 minutes with cold water, wringed out and subsequently skidded for 20 seconds. One rag was sealed wet, one was and hung for drying. Subsequently, both rags were evaluated for their smell by a panel.

The description of the odour was each: a nice flowery scent with woody undertone is noticed. The perfume composition appears complemented, harmonic, with an authentic scent.

The invention claimed is:

1. A fragrance composition comprising one or more compound(s) of formula (I)

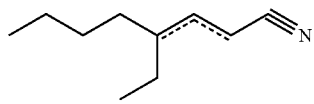

(I)

and one or more further fragrance(s),
wherein the weight ratio of the total amount of compound(s) of formula (I) to the total weight of further fragrance(s) is from 1:1000 to 1:0.1.

2. The fragrance composition according to claim 1, wherein the total amount of compound(s) of formula (I) is from 0.0001 to 99.9 wt.-%, relative to the total weight of the fragrance composition.

3. The fragrance composition according to claim 1, wherein the total amount of compound(s) of formula (I) is a sensorially effective amount.

4. The fragrance composition according to claim 1, wherein the one or more further fragrance(s) impart, modify and/or enhance one or more scents selected from the group consisting of green, nitrile, herbaceous, fresh, fruity, flowery, rosy, woody, sweet, earthy, fatty, metallic, balsam, iris, and carrot scents.

5. A perfumed product comprising:
(i) a fragrance composition according to claim 1, and
(ii) one or more further component(s).

6. A perfumed product according to claim 5, wherein the product is selected from the group consisting of washing and cleaning agents, hygiene or care products, cosmetics and home care products, products of decorative cosmetics, candles, lamp oils, joss sticks, insecticides, repellents, and propellants.

7. A perfumed product according claim 5, wherein the total amount of compound(s) of formula (I) is from 0.00001 to 10 wt.-%, relative to the total weight of the product.

8. A method for perfuming a product comprising:
(a) providing a fragrance composition according to claim 1, and
(b) adding the fragrance composition to the product in a sensorially effective amount.

9. A method for perfuming hair, skin, textile fibers, surfaces and/or room air comprising:
(a) providing a fragrance composition according to claim 1, and
(b) adding the fragrance composition to the hair, skin, textile fibers, surfaces and/or room air in a sensorially effective amount.

10. The method according to claim 9, wherein the fragrance composition comprises a surfactant.

11. The method according to claim 9, wherein the weight ratio of the total amount of compound(s) of formula (I) to the total amount of further fragrance(s) is from 1:1000 to 1:0.5.

12. The fragrance composition according to claim 1, wherein the weight ratio of the total amount of compound(s) of formula (I) to the total weight of further fragrance(s) is from 1:1000 to 1:0.5.

13. The fragrance composition according to claim 1, wherein the total amount of compound(s) of formula (I) is from 0.01 to 99 wt.-%, relative to the total weight of the fragrance composition.

14. The fragrance composition according to claim 1, wherein the total amount of compound(s) of formula (I) in the fragrance composition is sufficient for imparting and/or enhancing one or more scents selected from the group consisting of the scents green, nitrile, herbaceous, fresh, fruity, flowery, rosy, woody, sweet, earthy, fatty, metallic, balm, iris, and carrot scents.

15. The fragrance composition according to claim 1, wherein the total amount of compound(s) of formula (I) is sufficient for imparting and/or enhancing one or more scents selected from the group consisting of green, nitrile, rosy, iris, and carrot scents.

16. The fragrance composition according to claim 1, wherein the total amount of compound(s) of formula (I) in the fragrance composition is sufficient for imparting and/or enhancing one or more scents selected from the group consisting of rosy with iris and carrot scents.

17. The fragrance composition according to claim 1, wherein the one or more further fragrance(s) impart, modify and/or enhance one or more scents selected from the group consisting of green, nitrile, herbaceous, fresh, fruity, flowery, rosy, woody, sweet, earthy, fatty, metallic, balsam, iris, and carrot scents.

18. The fragrance composition according to claim 1, wherein the one or more further fragrance(s) impart, modify and/or enhance one or more scents selected from the group consisting of woody, fruity, and flowery scents.

19. The fragrance composition according to claim 1, wherein the one or more further fragrance(s) impart, modify and/or enhance one or more scents selected from the group consisting of fruity and flowery scents.

* * * * *